United States Patent [19]

Yamamoto et al.

[11] 4,373,818

[45] Feb. 15, 1983

[54] METHOD AND DEVICE FOR ANALYSIS WITH COLOR IDENTIFICATION TEST PAPER

[75] Inventors: Hiroshi Yamamoto; Yoshikazu Furutani, both of Kyoto, Japan

[73] Assignee: Kabushiki Kaisha Kyoto Daiichi Kagaku, Kyoto, Japan

[21] Appl. No.: 5,859

[22] Filed: Jan. 23, 1979

[30] Foreign Application Priority Data

Jan. 25, 1978 [JP] Japan .................................. 53-7638

[51] Int. Cl.³ .............................................. G01N 21/27
[52] U.S. Cl. ..................................... 356/408; 356/445
[58] Field of Search ............................... 356/445–448, 356/408, 416, 418, 421, 425, 402, 415, 422, 423, 409, 412

[56] References Cited

U.S. PATENT DOCUMENTS

| | | | |
|---|---|---|---|
| 2,451,501 | 10/1948 | Liben ................................ | 356/445 |
| 3,874,799 | 4/1975 | Isaacs et al. ...................... | 356/425 |
| 4,171,918 | 10/1979 | Mactaggart ........................ | 356/408 |

FOREIGN PATENT DOCUMENTS

| | | | |
|---|---|---|---|
| 1472092 | 3/1969 | Fed. Rep. of Germany ...... | 356/418 |
| 445009 | 10/1936 | United Kingdom ............... | 356/408 |
| 311185 | 8/1971 | U.S.S.R. ............................ | 356/402 |

*Primary Examiner*—Bruce Y. Arnold
*Attorney, Agent, or Firm*—Darby & Darby

[57] ABSTRACT

A method and apparatus are disclosed for an analyzer which measures concentration of a liquid specimen by monitoring the coloration of test paper which is either dipped into the specimen or is otherwise painted with it. In the method, inner stray rays produced by a light source which do not reach the test paper are experimentally monitored, so that the effect of such inner stray rays upon the accuracy of the test paper analysis is eliminated. Additionally, a method of relating relative reflectivity of the test paper to the concentration of the specimen is disclosed, in which method the calibration curve is modeled as a section of a hyperbola. In the apparatus, a microcomputer performs the evaluation and the detection of the coloration of the test paper and the compensation for various sources of instrumental error takes place electronically.

16 Claims, 14 Drawing Figures

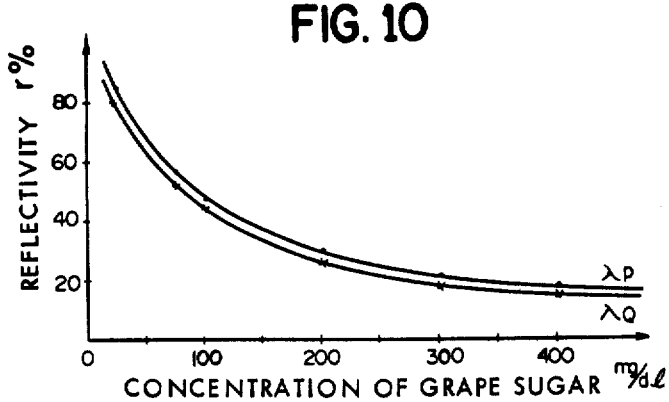
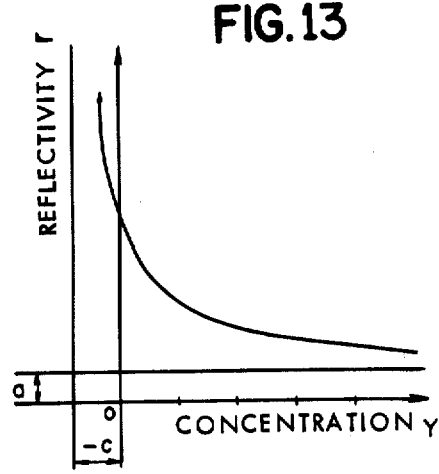
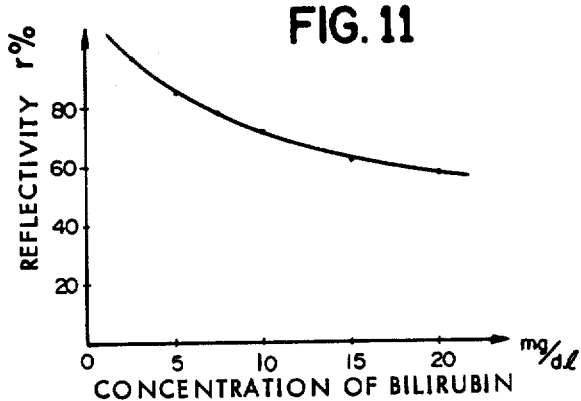
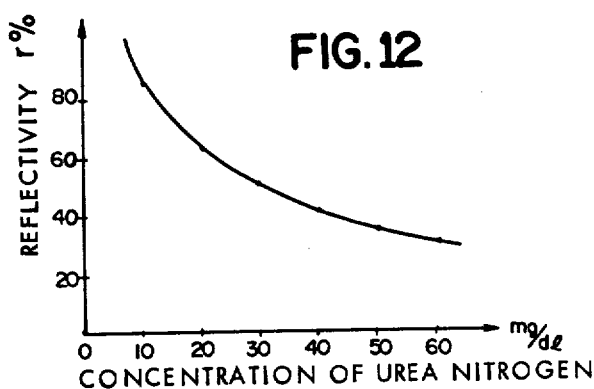

METHOD AND DEVICE FOR ANALYSIS WITH COLOR IDENTIFICATION TEST PAPER

BACKGROUND OF THE INVENTION AND PRIOR ART STATEMENT

This invention relates to a method and apparatus for quantitative analysis with color identification test paper.

Qualitative or quantitative analyses, conducted by a "Dip-and-Read" process with color identification test paper (hereinafter referred to as "test paper"), is widely used for such applications as the measurement of chemical constituents in blood and the screening examination of urine, and others by virtue of simplicity and ease of handling. Such analysis is particularly useful where rapid measurements or large numbers of measurements are required. When a technician performs the analysis by sight, the tone of coloration of the test paper painted with or dipped in the liquid to be examined is visually compared with standard color samples. This is suited for conducting only qualitative analysis, or, at best, rough quantitative analysis. In order to enhance to accuracy of quantitative analysis, it is necessary to employ some analyzing device or reflectivity meter which is capable of photoelectrically measuring the tone of coloration of the test paper. In recent years, therefore, along with the development and improvement of new types of test papers, there have been provided analyzers of various types, enabling a user to execute simplified and expeditious techniques of quantitative analysis on many samples.

Prior art analyzers provided until now operate with an indirect measuring method which measures a change of the reflectivity of the test paper photoelectrically, produces electric signals, and then converts the signals into differences of concentration by the application of a calibration curve. However, prior art analyzers are insufficiently accurate. Consequently, such analysis using test paper is said to be less accurate than titration and other methods of quantitative analysis, which latter methods are neither as simple nor as easy.

The principle of operation of these analyzers is based upon the fact that the reflection spectrum of the colored test paper should vary depending on the concentrations $Y_1$, $Y_2$, $Y_3$ of the target substance in the liquid to be examined, as shown in FIG. 1, wherein light with an appropriate wavelength, in particular with a wavelength or its adjacent one ($\lambda 0$ in FIG. 1), whose reflectivity changes markedly in accordance with the changes of the concentration, is selected when the change of the reflectivity of the test paper at the same wavelength is measured photoelectrically and indicated, being converted into units of concentration by reference to a calibration curve of the reflectivity versus concentration such as is shown in FIG. 2.

Of these types of analyzers, one is heretofore in wide use which is equipped (in the section assigned to the measurement of reflectivity) with an integrating sphere capable of efficiently measuring the reflected ray from the surface of reflection. FIG. 3 is a diagram of an example of the analyzers which use such an integrating sphere. The light from the light source 2 mounted on the upper part of the integrating sphere 1 is filtered to a predetermined wavelength through a filter 3 and irradiates the test paper 5 set under a specimen window 4 at the bottom of the integrating sphere. From the surface of the test paper 5 is reflected a quantity of light corresponding to the degree of coloration of the test paper. This reflected light reflects diffusively in the interior of the integrating sphere 1 and irradiates an optical detector 6 provided on a side face of the integrating sphere.

The magnitude of the reflected light represented by the output signal from the optical detector 6 passes through an amplifying-measuring circuit 7 and is indicated on the meter 8, which has a scale for direct reading of the concentration. In order to measure reflectivity, a standard reference signal must be established. In so doing, a relative reflectivity is obtained by comparing the magnitude of the reference signal with the magnitude of the output signal produced by the reflected light from the test paper. The input signal to the meter 8 is based on this relative reflectivity. There are various ways of establishing the reference signal: providing an electrical reference signal in advance, providing a standard of known reflectivity to enable the quantity of reflected light from the standard to be stored as a reference signal during measurement, and so on.

This type of prior art device has the following disadvantages:

1. It is constructed so as to photoelectrically measure the changes in reflectivity. Consequently, it is difficult to prevent the occurrence of dark current in the optical detector 6 and the offset voltage caused by the amplifier in the amplifying-measuring circuit 7. Dark current or offset voltage of photoelectric detectors also drift due to changes in their working temperature.

This drift can be fully corrected if the light from the light source 1 is interrupted by the use of, for example, a chopper or an intermittent light producing circuit, which has been already adopted in some devices. The influence of stray rays introducing into the integrating sphere 1 from outside also can be eliminated by the same means. In these cases, the fluctuations of the above-mentioned drift or the stray rays from outside must be, needless to say, small enough in comparison with the intermittent cycle of the flux of light.

2. The interior of the integrating sphere 1 is easily contaminated, since fibrous flocks of the test paper, dust from outside, or liquid to be examined can stick thereto. That causes the diffusion of the light to vary, causing the characteristics of the integrating sphere 1 to change during the course of long-time use. To prevent this contamination, a transparent plate 9 (such as sheet glass) is fitted into the specimen window 4 in order to prevent the intrusion of dust and the like into the interior. However, the operator must wipe off dirt on the outer surface of the transparent plate 9 before the measurement operation.

Such a transparent plate 9 on the specimen window 4 causes a problem in that a portion of the light which is supposed to reach the test paper 5 is reflected by the transparent plate 9 itself, generating inner stray rays which reach the optical detector 6. Even assuming that an object of 0% reflectivity were measured in conformity with the characteristics of the integrating sphere 1, detector 6 would still have a non-zero output. Therefore, the calibration curve of the output from detector 16 as compared to actual reflectivity does not pass through the origin. These inner stray rays vary, depending on the inclination of the transparent plate 9 with respect to the optic axis of incidence and also depending on the scattering of the incident light, which indicator and scattering vary between different analyzers. Hence, where test papers are measured in a reflectivity measuring system which has a transparent plate 9, different analyzers can yield different results, even though test papers of the same reflectivity were measured. This is shown in FIG. 4, in which Ro is the actual reflectivity of a standard of known reflectivity and the ordinate is relative reflectivity when corrected to Ro=100. The calibration curve passes through the origin in the case of a device M1 which has no inner stray rays, while the calibration curve deviates from the origin in devices M2 and M3 which have increasing amounts of stray rays.

There are other errors originating from other rays reflected by the inner parts of the optical system including the integrating sphere, such as the peripheral region of the specimen window 4, the shield plate, from the light from the light source and so forth. The inner stray rays caused by the latter can be excluded to some extent by changing the shape and structure of the optical system, e.g. by redesigning the integrating sphere. Still, some of these rays remain as an instrumental error, similar to the case of the inner stray rays discussed above. Consequently, the calibration curve is inaccurate. This brings about instrumental error, obstructing accurate analysis using test paper.

The conversion of relative reflectivity thus obtained into a directly readable concentration value is generally carried out by equipping meter 8 with a scale plate 10 having a nonlinear direct-reading scale, in analog form, this being calibrated into concentration, as is shown in FIG. 3. There is also another method, in which the measured output signal is corrected when it is compared with the reference signal so that both signals will be identical to each other. Here, the correction is determined by rotation of a potentiometer, and the concentration is read with the help of a scale plate attached to the potentiometer.

In either case mentioned above, however, the scale plates are paired with corresponding types of test papers to be examined. Accordingly, if the inner stray rays and the offset voltages differ between measuring devices, different kinds of scale plates should be provided on individual devices. This is impractical. Usually, devices share only one kind of scale plate having an engraved scale relative to one item to be examined. It is, thus, unavoidable that analyzers exist which have varying instrumental errors.

3. Even if an analyzer without any instrumental error could be made, it is impossible to fabricate test paper having a reflecting spectrum which is flat to all wavelengths of incident light. It is also inevitable that the wavelength of the light source will shift to some extent. If the wavelength of the light source shifts, the calibration curve changes, since the reflectivity of the test paper varies depending on wavelength, thereby resulting in other instrumental errors.

FIGS. 5 and 6 illustrate these problems. FIG. 5 illustrates the correlation between the reflecting spectra of the test papers at concentrations Y1, Y2, and Y3 at two different wavelengths ($\lambda 0$ and $\lambda 1$) of incident light thereby showing that the reflectivity r shifts with wavelength. FIG. 6 illustrates the different calibration curves of concentration with respect to reflectivity at the two different wavelengths $\lambda 0$ and $\lambda 1$ shown in FIG. 5.

The sources of error mentioned above vary from analyzer to analyzer at the time of manufacture. But even in the same analyzer, the intensity of light from the light source varies, and the wavelength fluctuates as the conditions of supply voltage, ambient temperature, and other parameters change both at the time of manufacture and later during use. This means that the characteristics of the analyzer itself change with the passage of time.

SUMMARY OF THE INVENTION

The invention has the object of improving the accuracy of analysis using test paper, and more particularly has the objects of solving the second and third problems listed above in such a manner that measurement of reflectivity will be made possible with high accuracy and without any instrumental error, of causing the concentration of the target substance to be indicated as a directly readable value in arbitrary units in digital form, and of making it easy to correct instrumental errors attributable to variance of wavelength, differences between the calibration curves originating from the dissimilarity of the samples, test papers, and so forth, thereby allowing quantitative analysis of high reliability.

In this invention, the first problem listed above is solved by taking off the difference between the output signal from the detector during the lighting of the light source and the output signal from the detector at the time the source is off while intermittently lighting the light source, thus eliminating the influences of dark current in the optical detector, the offset voltage in the amplifier, the outer stray rays, and so forth.

The second problem is solved as follows:

First, that portion of the output signal from the detector which is attributable to the inner stray rays is stored in each analyzer at the time of its manufacture, in the form of the proportion of the inner stray rays to the magnitude of the above-mentioned difference on a standard having a known reflectivity. This difference, taken on the standard, will be referred to hereinafter as the standard difference output signal. Next, during the correction and prior to measurement, that portion of the output signal from the detector which is attributable to inner stray rays is calculated from the above-mentioned proportion and the standard difference output signal at the time of the correction. The calculated portion is then substracted from the standard difference output signal and from the measured difference output signal which is taken from the colored test paper. These two quantities reflect the actual standard output signal and the actual measured output signal. Thus, instrumental error is reduced.

Referring to the third problem listed above, accurate quantitative measurement is made possible by functionally approximating the calibration curve with a function at the time of conversion into concentration and indicating the result on the meter, and by constructing the device to allow for correction of the divergence of the calibration curves which is attributable to shifting wavelength from the light source keeping the above function constant.

The invention will now be further described by reference to an exemplary preferred embodiment thereof, as illustrated in the drawings.

BRIEF DESCRIPTION OF THE DRAWINGS

FIGS. 8 and 9 are explanatory diagrams showing the correlation between the standard difference output signal, the inner stray rays output signal, and the reference output signal, in which FIG. 8 shows the case at the time of correction prior to use and in which FIG. 9 shows a comparison of the cases at the time of adjustment at manufacture and at the time of correction, respectively;

FIGS. 10, 11 and 12 show samples tested for grape sugar, bilirubin, and urea-nitrogen respectively; and FIGS. 13 and 14 are explanatory graphs showing cases where the calibration curves of concentration with respect to the reflectivity are approximately hyperbolic.

DETAILED DESCRIPTION OF THE PREFERRED EMBODIMENT

Figure 7:
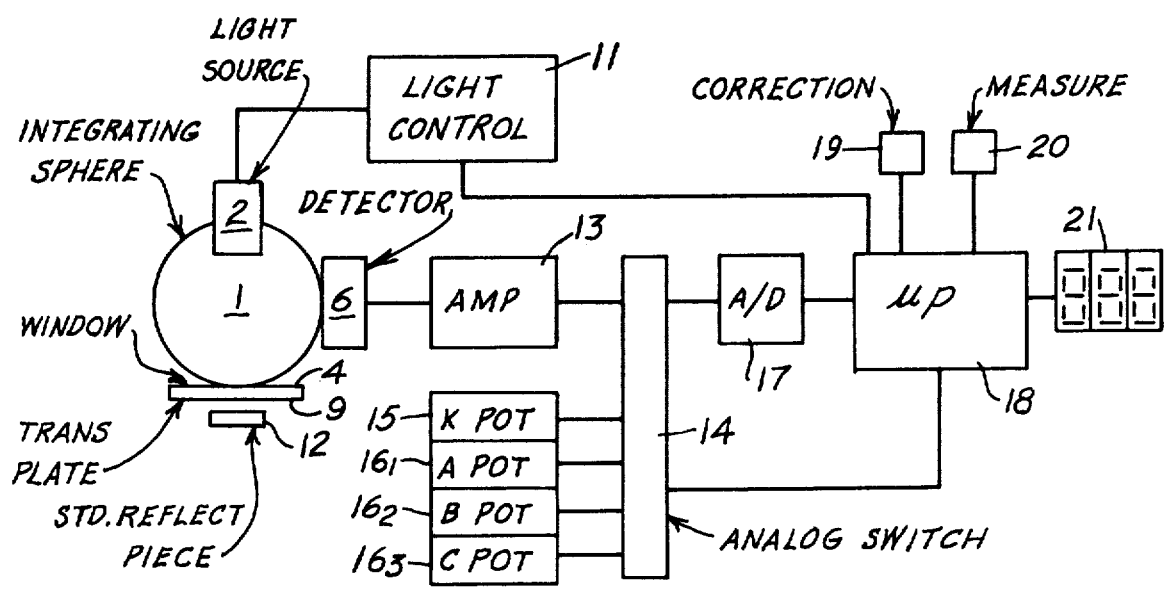
FIG. 7 is a block diagram of apparatus of the invention.

Referring first to FIG. 7, the light source 2 is intermittently lighted by means of a lighting circuit 11. In this case, the light source 2 can be a light-emitting diode (LED) or a tungsten-filament lamp paired with a filter, both having a peak near the wavelength suitable for the sample, and the like. It does not matter whether the light source 2 lights intermittently or whether its flux of light is interrupted.

Initially, a standard 12 of known reflectivity is set beneath the transparent plate 9 beneath the integrating sphere 1. On depression of the correction switch 19, the analog switch 14 is connected to the amplifier 13 by a command from the microcomputer 18. The output signal $R_{on}$ from detector 6 during lighting of the light source 2 and the output signal $R_{off}$ from detector 6 during darkening of the light source 2 is A-D converted by the A-D converter 17 and is stored in the memory of the microcomputer 18. The output signal $R_{off}$ during the darkening of light source 2 is composed of outputs arising from the dark current in the optical detector 6, the offset voltage of the amplifier 13, and the outer stray rays, which factors remain constant and can be eliminated through the substraction of output signal $R_{on}$ from output signal $R_{off}$—i.e. the generation of the standard difference output signal.

Figure 8:
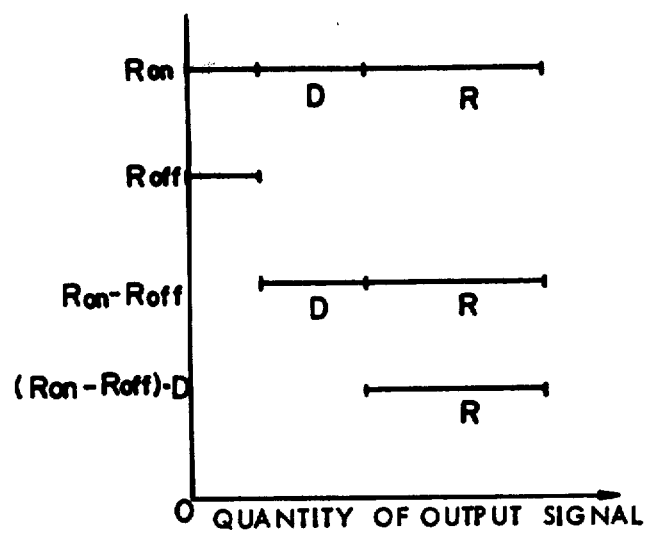

In this standard difference output signal ($R_{on}$-$R_{off}$), however, is included a component (the inner stray rays output signal) attributable to the inner stray rays produced in the interior of the integrating sphere 1, as shown in FIG. 8. The inner stray rays output signal D is a chief cause of the shifting of the characteristics of the analyzer. What remains after the subtraction of the inner stray rays output signal D from the standard difference output signal ($R_{on}$-$R_{off}$) is the standard output signal R—the end object of reflectivity measurement, as is seen in FIG. 8.

In the same fashion, what is left after the subtraction of the inner stray rays output signal D from the measured difference output signal ($S_{on}$-$S_{off}$) produced by using the test paper 5 in place of the standard 12 is measured output S. $S_{on}$ and $S_{off}$ are the output signals during the lighting and darkening of the light source respectively, during irradiation of the test paper.

The deviation of the inner stray rays output signal will now be set forth. As described above, the intensity of inner stray rays varies as a result of changes in the setting angle of the test paper and the material used in the transparent plate 9 (such as sheet glass) which is attached to the integrating sphere 1, the shape of the interior of the integrating sphere 1, the deflection of the optical axis of the light source 2 and the intensity of light therefrom and also varies as the intensity of the light source changes due to fluctuations in the supply voltage, temperature, aging and so on.

Since there are no changes in the relative positions of the structural elements of the photometric section (i.e., the integrating sphere 1, the light source 2, the measuring window 4, the transparent plate 9, the optical detector 6, and so on), and since there is no change in the reflection characteristics inside the integrating sphere 1, it is only the intensity of light from the light source which changes with the passage of time. Thus, this change occurs both in the standard difference output signal ($R_{on}$-$R_{off}$) during measurement of the standard 9 and also in the inner stray rays output signal D included therein. However, ratio k of the inner stray rays output signal D to the standard difference output signal ($R_{on}$-$R_{off}$) is kept constant. Having this fact in mind, the solution of the second problem has been accomplished.

Assuming that the analyzer is properly adjusted, its output will be zero when the reflectivity of the specimen is zero, or where, for example, nothing is put on the measuring section of the analyzer and the analyzer is placed intact in a dark room. On the other hand, the output of the analyzer when irradiating the standard yields a given standard value.

When the analyzer is properly adjusted, the measured difference output signal ($S_{on}$-$S_{off}$) during measurement of a reflectivity of zero expresses the inner stray rays output signal D exactly; and the standard difference output signal ($R_{on}$-$R_{off}$) is equivalent to the sum of the inner stray rays output signal D and the standard output signal R (FIG. 8).

In this case, the ratio k of the inner stray rays output signal to the standard difference output signal ($R_{on}$-$R_{off}$) can be expressed as a percent by the following equation:

$$k = \frac{D}{(R_{on} - R_{off})} \times 100\ (\%)$$

Conversely, when k is already known, then the magnitude of the inner stray rays output signal D can be found by the following equation:

$$D = (R_{on} - R_{off}) \times \frac{k}{100}$$

In case there are a plurality of analyzers (even though they are properly adjusted) the standard difference output signal will assume different values ($R_{on,1}$-$R_{off,1}$), ($R_{on,2}$-$R_{off,2}$), ($R_{on,3}$-$R_{off,3}$) . . . using only one standard owing to the variation between the respective light sources, optical detectors, etc. in separate devices. Likewise, the measured difference output signal of a sample having a reflectivity equal zero will vary since the inner stray rays output signal D can be D1, D2, D3 and so forth. Hence, the value of k does not generally stay constant and can be k1, k2, k3 . . . on account of the relative positions between the light source, optical detectors, etc.

Likewise, if the value of k is already known for an individual analyzer, D1, D2, D3 . . . can be determined separately on the basis of the following equations:

$$D1 = (R_{on,1} - R_{off,1}) \times \frac{k1}{100}$$

$$D2 = (R_{on,2} - R_{off,2}) \times \frac{k2}{100}$$

$$D3 = (R_{on,3} - R_{off,3}) \times \frac{k3}{100}$$

Thus, k can be found directly from both the measured difference output signal ($S_{on}$-$S_{off}$), measured with a reflectivity equal zero and from the standard difference output signal ($R_{on}$-$R_{off}$) during measurement of the standard. However, there is a simpler way to obtain k. This may be done by providing a second standard having a reflectivity different from the first standard, determining the reflectivity of the second standard relative to the first with the analyzer adjusted in advance, and using this result as the reference value to determine k. On the other hand, the reflectivity of the second standard relative to the first standard may be found on an arbitrary analyzer for which k is unknown. The value of the potentiometer k may then be adjusted empirically so that the measured reflectivity may coincide with the above-described reference value.

The reflectivity of the standard is not subject to any limitation and can have any suitable value at will, provided only that some common value is used for all individual analyzers.

Figure 9:
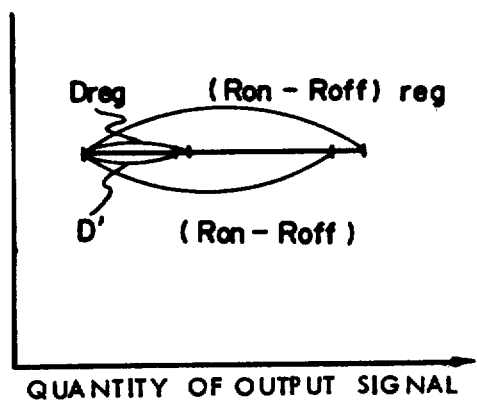

When the intensity of light changes after an adequate value of k has been once established in a given analyzer, the standard difference output signal from the standard varies from the value ($R_{on}$-$R_{off}$)$_{reg}$ at the time of the first adjustment to the value ($R_{on}$-$R_{off}$) in proportion to the change, as shown in FIG. 9, and the inner stray rays output signal also changes from $D_{reg}$ to D.

However, the proportion of $D_{reg}$ to ($R_{on}$-$R_{off}$)$_{reg}$ or D to ($R_{on}$-$R_{off}$) respectively has a constant value of k in either case, and conversely, when k is stored, it is possible to find the standard difference output signal ($R_{on}$-$R_{off}$) at the time it is corrected by the standard reflecting piece prior to measurement of the sample, and the inner stray rays output signal D can also be found through the ratio k.

In the inventive apparatus, k is made variable on the potentiometer K 15, and after the determination of the standard difference output signal ($R_{on}$-$R_{off}$), the resistance of potentiometer K 15 (which has been established in advance at an adequate value) is A-D converted by operating the analog switch 14. The product of k and the standard difference output signal ($R_{on}$-$R_{off}$) is computed by the microcomputer 18 on the basis of the following equation:

$$D = \frac{k}{100} (R_{on} - R_{off})$$

The inner stray rays output signal D thus obtained is stored in the memory of the microcomputer 18.

Next, after the test paper 5 (painted with or impregnated in the liquid to be examined) is set beneath the transparent plate 9 beneath the integrating sphere 1, the measuring switch 20 is operated. The analog switch 14 is then thrown under the control of the microcomputer 18, the output signal $S_{on}$ (during the new lighting of the light source 2) and the output signal $S_{off}$ (during the darkened period of the light source 2) are A-D converted by the A-D converter 17, thus enabling the measured difference output signal ($S_{on}$-$S_{off}$) to be obtained.

The subtraction of the inner stray rays output signal D stored in the above memory from the measured difference output signal yields the measured output signal. Afterwards, the relative reflectivity (r %) is calculated on the basis of the following equation:

$$r (\%) \frac{S}{R} \times 100 = \frac{(S_{on} - S_{off}) - D}{(R_{on} - R_{off}) - D} \times 100 \quad (1)$$

The relative reflectivity calculated in this way is independent on the influence of the dark current in detector 6 or the offset voltage of amplifier 7 and can correct the inner stray rays output (which is different in each analyzer) so that it becomes possible to obtain an analyzer which has no instrumental error for quantitative analysis with test paper.

The coloration characteristics of various kinds of test papers were investigated on the basis of many experimental results. The results of several tests on the calibration curve expressing the correlation between the concentration of the specimen substance and the reflectivity of the test paper, are shown in FIGS. 10 to 12. Using these, a further study was undertaken to approximate these calibration curves by a simple function.

FIG. 10 gives the correlation between the concentration (mg/dl) of grape sugar and the reflectivity (r %) of the test paper used for its analysis. Grape sugar is oxidized by an oxidizing enzyme of grape sugar to be changed into gluconic acid and hydrogen peroxide. The coloration indicator is oxidized and colored by hydrogen peroxide thus produced and peroxidase. Two graphs separately express wavelengths of $\lambda p = 670$ nm and $\lambda Q = 660$ nm, which were used.

FIG. 11 shows the correlation between the concentration (mg/dl) of bilirubin and the reflectivity (r %) of the test paper used for its analysis. Here, bilirubin acts on a diazo reagent in an acidic condition and the coloration of the thus produced azobilirubin is measured by light having a wavelength of 550 nm.

FIG. 12 shows the correlation between the concentration (mg/dl) of urea nitrogen and the reflectivity of the test paper used for its analysis. Here, urea is decomposed into ammonium carbonate by the use of urease, and the indicator is then colored through the utilization of the changeability of hydrogen ion concentration by dint of ammonium thus produced. The wavelength used here is 620 nm.

In the analysis dependent on the coloration, the transmission of the light through the coloring substance is frequently measured to determine the degree of extinction. If the incident light on the coloring substance is Io and the light transmitted therethrough is I, the latter is expressed by the equation: $I = Ioe^{Ecl}$ (an exponential function) in which c denotes the concentration, E denotes the degree of extinction and l denotes the optical path length. The degree of extinction E is expressed by the equation: $E = \ln(Io/I) = Ecl$, and is proportional to the concentration C.

In comparison, the light reflected from the test paper is composed both of the light returned to the surface of the test paper and the light diffused on the surface of the test paper as a result of absorption into or scattering over the test paper. It follows that, unlike the transmitted light I, this reflected light cannot be expressed as an exponential function since it has been absorbed, at least to a degree. However, when the definition of the approximation function was modified and the range of concentration was limited to that needed for practical use by way of experiment, the calibration curves shown in FIGS. 10–29 all fit an exponential function in the form of $Y = \alpha e - \beta r + \gamma$, wherein Y denotes the concentration of the specimen substance, r denotes the reflectivity and $\alpha, \beta, \gamma$ are constants.

Further, under these conditions (namely, where the definition of the approximation function was modified and the range of concentration was limited to that needed for practical use) it was found that the calibration curves shown in FIGS. 10 to 12 could be regarded as segments of a hyperbola in a simple form, and that the relationship between concentration Y and reflectivity, r, could be expressed as:

$$Y = \frac{b}{r-a} + C \quad (II)$$

a, b and c being constants.

Thus, the correlation between the concentration Y and the reflectivity r corresponding to FIGS. 10 to 12 can be approximated by assigning appropriate values to each of the constants a, b, and C in equation (II), as shown in Tables 1 to 4, and the conversion of the reflectivity r into the concentration Y can be performed in this way with an error of plus or minus only several percent.

In Tables 1 to 4, the concentration shown is the theoretical concentration of a solution, the approximate value is the concentration found by the use of the appropriate approximation equation from the reflectivity r of the solution, and the percentage of error is the difference between the approximate concentration and the theoretical concentration in proportion to the theoretical concentration. In the examples, each percentage error exhibits a good approximation—under 4%. Even if the calibration curves decrease monotonically among test papers used in the other measurements, the calibration curves can be approximated by the use of equations in the form of equation (II), wherein r denotes the reflectivity after correction by an adequate standard output signal, and a, b, C are the constants which define the forms of the calibration curves.

TABLE I

| Concentration mg/dl | Reflectivity % | Approximate Value mg/dl | Percentage of Error |
|---|---|---|---|
| 25 | 85 | 24.9 | −0.40 |
| 75 | 56 | 74.3 | −0.93 |
| 100 | 47 | 102.0 | 2.00 |
| 200 | 30 | 199.3 | −0.35 |
| 300 | 22 | 296.5 | −1.17 |

TABLE I-continued

| Concentration mg/dl | Reflectivity % | Approximate Value mg/dl | Percentage of Error |
|---|---|---|---|
| 400 | 17 | 403.1 | 0.78 | test paper for analysis of grape sugar (FIG. 10) measuring wavelength $\lambda p = 670$ nm approximate equation:
$$Y = \frac{8170}{r + 0.23} - 71.0$$

TABLE 2

| Concentration mg/dl | Reflectivity % | Approximate Value mg/dl | Percentage of Error |
|---|---|---|---|
| 25 | 80 | 25.6 | 2.40 |
| 75 | 52 | 72.9 | −2.80 |
| 100 | 43 | 100.5 | 0.50 |
| 200 | 26 | 200.4 | 0.20 |
| 300 | 18 | 305.1 | 1.70 |
| 400 | 14 | 395.7 | −1.08 | test paper for analysis of grape sugar (FIG. 10) measuring wavelength $\lambda Q = 660$ nm approximate equation:
$$Y = \frac{7571}{r + 2.39} - 66.3$$

TABLE 3

| Concentration mg/dl | Reflectivity % | Approximate Value mg/dl | Percentage of Error |
|---|---|---|---|
| 2.5 | 97 | 2.5 | 0 |
| 5.0 | 85 | 5.2 | 4.00 |
| 7.5 | 78 | 7.4 | −1.33 |
| 10.0 | 72 | 9.8 | −2.00 |
| 15.0 | 63 | 15.3 | 2.00 |
| 20.0 | 58 | 19.9 | −0.50 | test paper for analysis of bilirubin (FIG. 11) measuring wavelength $\lambda = 550$ nm approximate equation:
$$Y = \frac{794}{r - 31.04} - 9.6$$

TABLE 4

| Concentration mg/dl | Reflectivity % | Approximate Value mg/dl | Percentage of Error |
|---|---|---|---|
| 10 | 86 | 10.0 | 0 |
| 20 | 63 | 20.4 | 2.00 |
| 30 | 51 | 29.3 | −2.33 |
| 40 | 41 | 40.4 | 1.00 |
| 50 | 35 | 49.8 | −0.40 |
| 60 | 30 | 60.2 | 0.33 |

Test paper for analysis of urea nitrogen (FIG. 12) measuring wavelength $\lambda = 620$ nm approximate equation:
$$Y = \frac{2730}{r + 3.88} - 66.3$$

Figure 1:
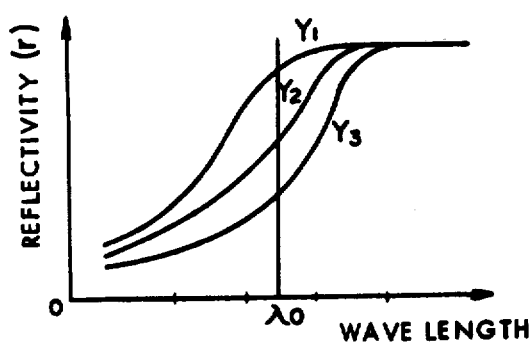
FIG. 1 is a graph of the reflection spectra of the test papers colored by liquid specimens of different concentrations.
Figure 2:
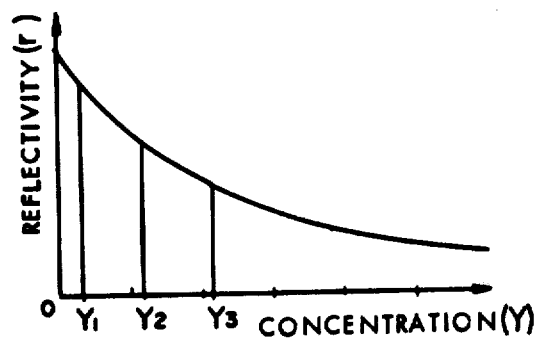
FIG. 2 is a graph of the calibration curve of concentration with respect to reflectivity at wavelength $\lambda 0$ obtained from the coloration characteristics of the test papers in FIG. 1.
Figure 3:
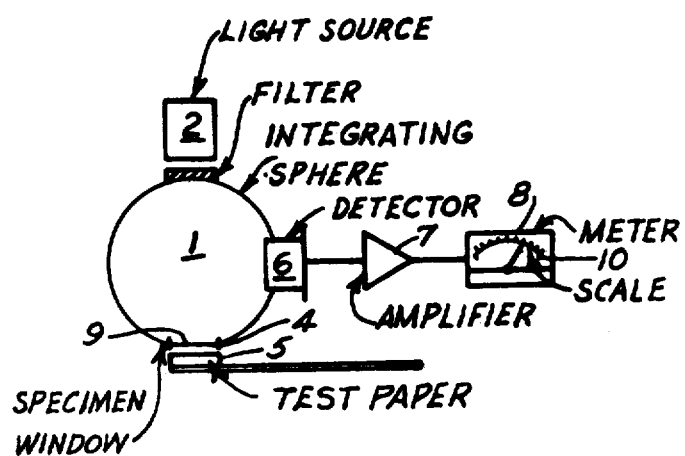
FIG. 3 is an explanatory schematic view of a conventional analyzer.
Figure 4:
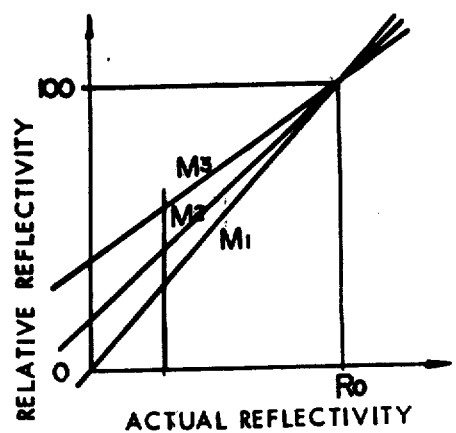
FIG. 4 is a graph of the calibration curves of the actual reflectivities of standard reflecting pieces and their relative reflectivities corrected in analyzers having varying amounts of inner stray rays.
Figure 5:
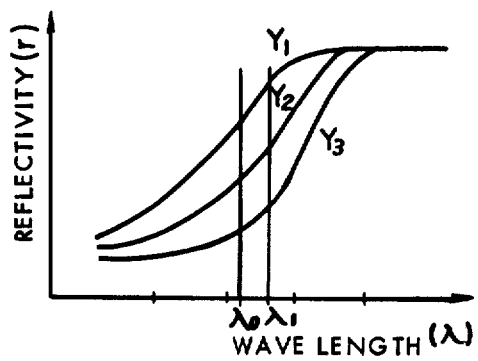
FIG. 5 is a graph of the reflection spectra of test papers colored by liquid specimens of different concentrations, similar to FIG. 1.
Figure 6:
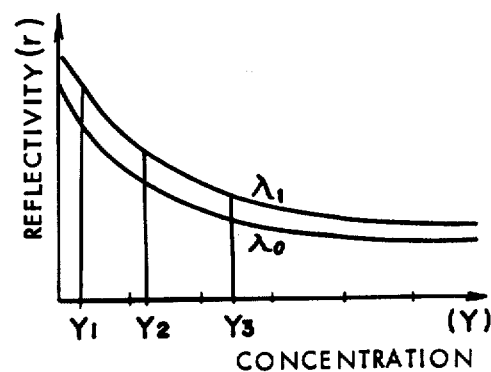
FIG. 6 is a graph of the calibration curves of concentration with respect to reflectivity at wavelengths λ0 and λ1 obtained from the coloration of the test papers having reflection spectra shown in FIG. 5.

Here, referring to the correlation between the concentration Y and the reflectivity r, it is possible to shift the origin of the appropriate equation of the calibration curve to the coordinates by varying the constants an and/or C, as shown in FIG. 13, and to make the calibration curve pass parallel to the coordinate axis, or else to make the shape of the calibration curve variable by changing the constant b, as shown in FIG. 4.

These constants a, b, and C, like the constant k, are held in analog form in potentiometer A $16_1$, potentiometer B $16_2$, and the potentiometer C $16_3$, respectively. The values of these constants a, b, and C are variable depending on the sorts of items to be measured and the test papers, thereby enabling the slight difference between the calibration curves to be corrected with facility. This effectively equips an analyzer with a plurality of calibration curves simultaneously when correcting instrumental errors caused by shifting of the wavelength of the light source although only one kind of test paper is used. This produces satisfactory results and helps to produce an analyzer of simple construction and of great versatility. However, the constants a, b, and C change, accordiang to the kinds of specimens and test papers, so that it is necessary to use several sets of potentiometers $16_1$, $16_2$, and $16_3$ in order to analyze a plurality of specimens in the same analyzer simultaneously.

It may be remarked in this connection that when complex functions are programmed into the microcomputer 18 and other computers, it becomes difficult to reduce the number of program steps, or to shorten the operation time, since the capacity of memory decreases. Consequently, it is far better to perform the calculations using equation II as compared with using the exponential function $Y = \alpha e - \beta r + \gamma$.

Where the reflectivity r has been calculated without any instrumental error, as mentioned above, each of the constants a, b, and C are A-D converted under the control of the microcomputer 18 as in the case of k. The concentration Y is determined by equation (II) and is indicated as a directly readable digital value on an indicating means such as the numerical indicator 21. At this time, the instrumental error of the calibration curve produced by a slight difference from the wavelength used can be eliminated if each of the constants a, b, and C has been adjusted at the time of manufacture by using a color standard which has a standard coloration, thereby enabling the concentration to be directly readable in a simple operation and without any instrumental error. Even if constants a, b, and C in a device have been properly adjusted, there is still the possibility that the wavelength will vary slightly during use, e.g. by changes of supply voltage or ambient temperatures. In such a case, it is only necessary to adjust either constant a or C on the potentiometer A $16_1$, or C $16_3$.

These examples show the cases where all of the constants k, a, b, and C are stored in the potentiometers in analog form. It does not matter whether these constants are held beforehand in the memory of the microcomputer as a plurality of numerical tables in digital form, or directly inputted from external memory elements, such as magnetic cards together with other data. The invention can also be used where a means for the measurement of reflected light other than the integrating sphere, for example, such as a means for measuring the quantity of reflected light in a fixed direction by impinging the flux of light on the reflecting surface at a specified angle, is employed in the photometric section.

Further, the correction for the effect of inner stray rays performed according to the invention can be applied when reflectivity in general is to be measured, and is not limited merely to the measurement of reflectivity with colored test papers.

The method of analysis according to the invention makes it possible to achieve exact measurement of the relative reflectivity while eliminating the influence of the inner stray rays in finding the reflectivity of a colored test paper painted with or impregnated in the liquid to be examined, by calculating the inner stray rays output signal at the time of measurement from the proportion of the inner stray rays output signal to the standard reference output signal stored beforehand and the quantity of standard difference output signal at the time of the correction prior to the measurement, and by applying the correction to both the standard and the measured difference output signals.

The method according to the invention makes it further possible to correct the fluctuation of the calibration curves due to scattering and change of wavelengths of the source, and to convert the reflectivity into the concentration accurately without any scattering by approximating the calibration curves to be parts of hyperbolae, and by adjusting the constants in the formula of the conversion.

The device according to the invention is able to correct the proportion of the inner stray rays output signal to the standard difference output signal and also each of the constants in the formula of the conversion as the approximate equation at the time of storing both of them in the potentiometers in analog form, thereby making possible the accurate quantitative measurement of the concentration of the specimen substance in the form of a digital display, by entirely eliminating the influence both of the inner stray rays produced in the photometric section and the influence of the fluctuation of the intensity of light from the light source, by completing the set of characteristics in the capacity of the reflectivity meter without any instrumental error, and by removing the instrumental error caused by scattering of the wavelength of the light from the light source.

What we claim is:

1. A method for analyzing concentration of substance under analysis in an electronic analytical instrument having a light source, which method determines the concentration by measuring, at at least one wavelength of interest, light reflected from a test piece of paper bearing the substance and light reflected from a standard having a known reflectivity, and by forming a ratio of these measurements, which ratio is corrected for light source intensity variations and for inner stray rays, said ratio being termed the relative reflectivity of the test piece, said method comprising the steps of:
    determining a constant of the instrument useful in correcting the instrument for the effects of light source intensity variations and inner stray rays;
    storing said constant electronically;
    using the stored constant to determine a value proportional to the detected inner stray rays; and
    using said value to determine the relative reflectivity of the test piece.

2. The method defined by claim 1, further including the step of calibrating the instrument by using two standards having a known relative reflectivity and adjusting the instrument to indicate said known relative reflectivity while comparing light reflected from one standard with light reflected from the other standard.

3. The method defined by claim 1 further comprising the step of calibrating the instrument by:
    establishing a standard quantity by intermittently illuminating the standard with light and subtracting light output detected during a period of non-illumination of the standard from light output detected during a period of illumination of the standard, whereby a correction for dark current, outer stray rays and amplifier offset is accomplished;
    establishing an inner stray rays constant from light output detected during illumination of a totally non-reflective standard, whereby a correction for inner stray rays is accomplished;
    establishing a test quantity by intermittently illuminating the test piece with light and subtracting light output detected during a period of non-illumination of the test piece from light output detected during a period of illumination of the test piece; and computing relative reflectivity of the test piece using the standard quantity, the test quantity, and the constant.

4. The method defined by claim 2 or 3, further comprising the step of converting the relative reflectivity of the test piece into concentration of the substance.

5. The method defined by claim 4, wherein said step of converting is carried out in accordance with an equation in which $$Y = \frac{b}{r-a} + C$$

where
Y = concentration of the substance
r = the relative reflectivity of the test piece and
a, b, and C are empirically derived constants.

6. An electronic apparatus for analyzing concentration of a substance under analysis and which measures the concentration by measuring light reflected from a test piece of paper bearing the substance and light reflected from a standard having a known reflectivity by forming a ratio which is corrected for light source intensity variations and inner stray rays, said ratio being termed the relative reflectivity of the test piece, said apparatus comprising:
  optical means for irradiating an object with light of a predetermined wavelength;
  a second means for producing a constant signal which corresponds to a constant of the instrument useful in determining inner stray rays present during irradiation of the object;
  means for electronically storing the constant signal;
  means for detecting light reflected from the object during irradiation and for producing a first signal and a second signal which correspond, respectively, to light reflected off the test piece and light reflected off the standard;
  means for deriving from the stored constant signal a correction signal representing inner stray rays present during irradiation of the object; and
  a fourth means for determining the relative reflectivity of the test piece in response to the correction signal, the first signal and the second signal, in a manner such that the relative reflectivity of the test piece is corrected for effects of light source intensity variations and inner stray rays.

7. The apparatus defined by claim 6, wherein the fourth means comprises computer means.

8. The apparatus defined by claim 7, wherein the correction signal, the first signal and the second signal are all analog signals, wherein the computer means is a digital computer means, and wherein the fourth means includes an analog to digital converter which converts the correction signal, the first signal and the second signal into digital signals for application to said computer means.

9. The apparatus defined by claim 8, wherein the computer means includes means for storing the constant signal prior to detecting light reflected from the test piece.

10. The apparatus defined by claim 6, further comprising a means for converting the relative reflectivity of the test piece into a corresponding concentration of the substance.

11. The apparatus defined by claim 10, further comprising a means for storing the corresponding concentration of the substance as a concentration signal.

12. The apparatus defined by claim 11, wherein the concentration signal is derived in accordance with an equation in which:

$$Y = \frac{b}{r-a} + C$$

where:
Y = concentration of the substance
r = the relative reflectivity of the test piece and
a, b and C are empirically derived constants.

13. The apparatus defined by claim 12, wherein the concentration signal is a digital signal.

14. The apparatus defined by claim 10, wherein the fourth means comprises a computer.

15. The apparatus defined by claim 14, wherein the correction signal, the first signal and the second signal are all analog signals, wherein the computer is a digital computer, and wherein the fourth means includes an analog to digital converter which converts the correction signal, the first signal and the second signal into digital signals for application to the computer.

16. The apparatus defined by claim 6, wherein the optical means includes a means for interrupting irradiation of the object.

* * * * *